United States Patent [19]

Teichner et al.

[11] 3,963,646

[45] June 15, 1976

[54] METHODS FOR THE MANUFACTURE OF COMPOSITE CATALYSTS CONTAINING A COMPOSITION OF A TRANSITION METAL ON A SUPPORT

[75] Inventors: Stanislas Teichner; Gérard Gardes, both of Villeurbanne, France

[73] Assignee: Agence Nationale de Valorisation de la Recherche (ANVAR), Neuilly-sur-Seine, France

[22] Filed: Aug. 2, 1973

[21] Appl. No.: 384,836

[30] Foreign Application Priority Data

Aug. 18, 1972  France ............................ 72.29580

[52] U.S. Cl. ............................ 252/459; 252/466 J; 252/472; 260/597 R; 260/683.65; 260/667
[51] Int. Cl.² .................... B01J 29/10; B01J 29/20
[58] Field of Search ................ 252/459, 466 J, 472

[56]  References Cited
UNITED STATES PATENTS

| | | | |
|---|---|---|---|
| 3,547,830 | 12/1970 | Shropshire | 252/466 J X |
| 3,551,352 | 12/1970 | Carr et al. | 252/459 X |
| 3,591,649 | 7/1971 | Kroll et al. | 252/459 X |
| 3,637,529 | 1/1972 | Van Beck et al. | 252/466 J X |
| 3,752,773 | 8/1973 | Duke et al. | 252/459 X |
| 3,781,350 | 12/1973 | Fujita et al. | 252/472 X |

FOREIGN PATENTS OR APPLICATIONS 1,568,817   5/1969   France ............................ 252/459 UX

*Primary Examiner*—Paul F. Shaver
*Attorney, Agent, or Firm*—Larson, Taylor and Hinds

[57]  ABSTRACT

Starting from hydrolysable salts of at least one transition metal and at least one metal giving a refractory oxide in solution in a non-aqueous solvent, simultaneous hydrolysis of the salts is produced by the addition of an amount of water which corresponds substantially to that necessary for the stoichiometry of the reactions. Drying of the coprecipitate formed is effected in an autoclave under hypercritical conditions. Hydrogenation or controlled oxidation catalysts of greater activity are thereby produced.

12 Claims, No Drawings

METHODS FOR THE MANUFACTURE OF COMPOSITE CATALYSTS CONTAINING A COMPOSITION OF A TRANSITION METAL ON A SUPPORT

The invention relates to a method for the manufacture of a composite catalyst containing a transition metal deposited on a support, and it relates especially, because it is in their case that its application seems to offer the most advantage, to catalysts containing iron, cobalt or, more particularly again, nickel in the state of the metal or oxide. Nickel oxide catalysts are used particularly in oxidation reactions and reduced nickel catalysts in hydrogenation reactions which will be designated for convenience of expression oxygenation catalysts or hydrogenation catalysts.

It is known that the catalytic activity of such catalysts is in general tributary to their specific surfaces. Also there have already been proposed methods for the production of catalysts, particularly based on nickel, utilising coprecipitation of a nickel oxide and of another oxide, especially a refractory oxide of high porosity, so as to produce a dispersion of the nickel on the porous support thus obtained, then thermal dehydration of the coprecipitate and — in the case where a catalyst is required containing nickel in the metallic state — a reduction of this coprecipitate.

These last operations which required generally high temperatures are however accompanied often by a change in the textural and structural appearance of the catalyst which often acts contrary to the desired purpose.

It is therefore an object of the invention to overcome these drawbacks, especially to provide a method for the preparation of composite catalysts of the type concerned in which the dehydration steps and, if necessary, reduction steps which follow the operation of coprecipitation of a hydroxide of the transition metal, especially nickel, and of a hydroxide of the refractory metal, maybe effected at a sufficiently low temperature and under conditions such that they do not involve a modification of the structural appearance of the coprecipitates formed.

The method according to the invention is characterised by the fact that, starting from hydrolysable salts of at least one transition metal and of at least one metal giving a refractory oxide, in solution in a non-aqueous solvent, simultaneous hydrolysates are produced of these salts by the addition of a sufficient amount of water for this purpose and that the drying of the coprecipitate formed is effected in an autoclave under hypercritical conditions.

The amount of water used for the abovesaid hydrolyses corresponds substantially to that which is necessary for the stoichiometry of the reactions.

The reaction medium obtained is transferred to the inside of a closed autoclave at a temperature enabling the hypercritical conditions to be reached in the presence of an amount of solvent sufficient for this purpose, and when the hypercritical conditions are reached, removal of the solvent vapors is effected.

The metals of the hydrolysable salts which are utilised, belong to group VIII of the periodic classification, and are constituted preferably by nickel, iron or cobalt, more particularly by nickel.

The salt of the refractory metal used is a salt of aluminum, of silicon or of magnesium.

The abovesaid salts are constituted by alcoholates or acetates of the metals concerned, and the hydrolysable medium is constituted by a homogeneous water-alcohol mixture or by a heterogeneous water-toluene mixture.

The drying of the coprecipitate in the autoclave is effected in a reducing atmosphere.

It is indicated that the ratio of the number of atoms of metal of the catalyst substance to the number of atoms of the refractory substance is comprised between 1/5 and 1, especially between 1/5 and 3/5.

In a preferred embodiment of the invention, there are adopted the conditions described in French Patent No. 1,568,817 filed 30 Nov. 1967 in the names of Teichner and Nicolaon and relating to the preparation of mineral aerogels, especially based on silicon, from hydrolysable organic compounds in a non-aqueous and volatile solvent, such as methanol, treated in the autoclave and under conditions of temperature and pressure such that the critical point of the methanol is reached and even exceeded.

This method, which relies on the hydrolysis of alcoholic solutions of metals, has the advantage of not involving recrystallisation, nor a change in structure of the gel formed at the moment of removing the solvent. It is noted that the use of the method of preparing aerogels, applied to the manufacture of a mixed oxide — of two or several metals of which one especially is a transition metal and the other a refractory metal, preferably, alumina, silica and magnesia — lead to the obtaining of a catalyst of high specific surface and high catalytic activity.

It was noted that metallic nickel could be obtained (or any other metal of the nickel group) directly by reduction in the autoclave at a temperature distinctly lower than the normal reduction temperature. Under these conditions of temperature, the grains of nickel remain finely dispersed on the surface of the support and do not undergo increase in size nor reduction in useful surface.

The method according to the invention has enabled the obtaining of oxygenation or hydrogenation catalysts under conditions such that the textural characteristics of the solids obtained are close to those of gels impregnated with solvent, that is to say of very high specific surface; and of conferring on the catalyst thus constituted properties such that they respond to the various exigencies of practice better than hitherto.

The invention also relates to an improved method of carrying out catalytic reactions by means of the improved composite catalyst obtained by the method according to the invention, for example, controlled oxidation, dimerisation or hydrogenolysis reactions.

The invention will be better understood by means of the additional description which follows, as well as of the examples below, which description and examples relate to preferred embodiments of the invention, not to be considered in any way limiting.

EXAMPLE 1

To establish ideas the case is first taken of a catalyst of mixed metallic oxides comprising a single refractory element, alumina as support and nickel oxide as catalytic base.

The first step is carried out by hydrolysis of an alcoholic solution of secondary aluminum-butylate and hydrated nickel acetate.

For this, 2.5 g of secondary aluminum butylate are dissolved in butanol-2 in a sufficient amount to obtain 20 g of solution. There are then added with vigorous stirring 5 g of a 10% solution by weight of hydrated nickel acetate in methanol, and in which there is added an amount of water such that the stoichiometries of the reactions below are respected (In the amount of water to be added, account is taken of the water introduced by the nickel salt).

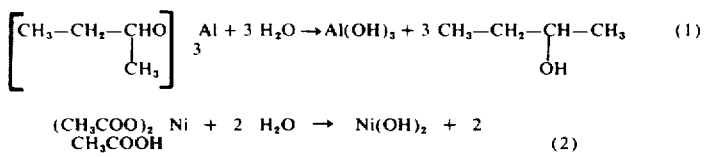

$$(CH_3COO)_2 Ni + 2 H_2O \rightarrow Ni(OH)_2 + 2 CH_3COOH \quad (2)$$

The precipitation is immediate at ambient temperature. Stirring is maintained for 5 minutes, then the container holding the gel is transferred into a autoclave of 300 ml, after having provided it with a U-tube. 150 ml of butanol-2 are added intended to reach hypercritical conditions, the autoclave is closed and the rise in temperature is started.

As soon as the hypercritical conditions are reached, the removal of the solvent is commenced, then the apparatus is purged of alcohol vapors by a flow of dry nitrogen for several minutes, is allowed to cool and the catalyst is withdrawn.

In the above example, the ratio of the number of atoms of nickel to the number of atoms of aluminum is equal to 1/5. With this method, solids can be obtained of which the ratios Ni/Al can reach 2/5 and 3/5. In order that the catalyst may retain its efficiency, it is advisable not to let the value of this ratio drop below 1/5. In addition, this value is that for which the specific surface of the solid is highest and it is observed that it cannot be increased without causing a distinct reduction in the macroporous volume (or porous volume measured by mercury porosimetry) of the aerogels, as shown in the Table below.

TABLE 1

| Specimens | 1 | 2 | 3 |
|---|---|---|---|
| Ratio Ni/Al | 1/5 | 2/5 | 3/5 |
| S m²/g | 710 | 590 | 480 |
| $V_p$ cm³/g | 11 | 7.1 | 5.8 |
| $V_{p_N}$ cm³/g | 1.8 | 1.65 | 1.7 |

S specific surface measured by the BET method
$V_{p_N}$ porous volume measured by a nitrogen absorption at the temperature of liquid and nitrogen (pores of diameter less than 840 A)
$V_p$ porous volume measured by mercury porosimetry (pores of diameter greater than 580 A)

In this Table, it is noted that the specific surface of the solids which emerge from the autoclave is very great since it reaches 500 to 700 m²/g and these values are little modified when the Ni/Al ratio increases, as well as that of the micro porous volume (porous volume measured by nitrogen absorption).

The catalytic activity is determined in the course of a controlled (i.e. mild) oxidation reaction of a $C_4$ hydrocarbon (isobutylene), and of a catalyst (nickel oxide - alumina) of which the Ni/Al ratio is 3/5. The partial oxidation products are acetone and methylacrolein according as 1 or 2 molecules of oxygen take part in the reaction; it is sought to minimise the secondary oxidation products CO, $CO_2$ and $H_2O$.

A first test is carried out without any previous treatment of the catalyst, that is to say without treatment by water vapor as is the case most frequently with controlled oxidation catalysts. The conditions produced in the course of this catalytic test are the following:

| | |
|---|---|
| Total pressure of the reactants | 1 atmosphere |
| Composition of gases | 62.5% isobutylene |
| | 37.5% oxygen |
| Total flow rate of reactants | 1.6 l/h. |
| Contact time | 0.78 second |
| Reaction temperature | 245°C |

An operation duration of 200 minutes must be attained for the catalytic activity relative to the reaction products to become stationary. In the stationary condition, the yield of oxidation products is then:
60% of methylacrolein
23.5% of acetone
16.5% of $CO_2$
0% of CO.

The controlled oxidation reactions giving rise to the formation of methylacrolein and acetone according to the reactions below (3) and (4) introduce a yield of $CO_2$ in the neighbourhood of 7.8%; the yield of 16.5% of $CO_2$ shows that the total oxidation reaction (5) has not been able to be completely avoided in the course of this test.

Controlled oxidation reactions:

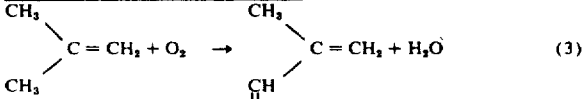

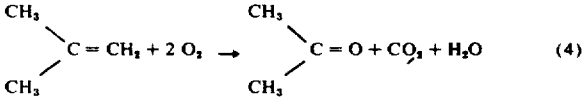

Total oxidation reaction:

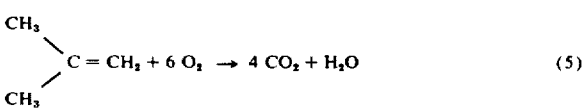

On the same catalyst and for the same ratio of the number of Ni/Al atoms, a second catalytic test is carried out with preliminary treatment. In the course of this treatment, there is caused to pass over the catalyst a mixture of oxygen and water vapor at atmospheric pressure for 24 hours and at 250°C ($P_{H_2O}$ = 55 torr). The reaction conditions of the catalytic test are as follows:

| | |
|---|---|
| Total pressure of reactants | 1 atmosphere |
| Composition of the gases | 62.5% isobutylene |
| | 37.5% oxygen |
| Total flow rate of reactants | 1.6 l/h |
| Contact time (catalytic reactants) | 0.64 second |
| Temperature | 256°C |

The yields of controlled oxidation products are then:
66.5% of methylacrolein
25% of acetone 8
8.5% of CO and $CO_2$.

The new values for the yield show that the thus treated catalyst has nil activity with respect to complete oxidation leading to the formation of $CO_2$, according to the reaction (5). The percentage, CO, $CO_2$ formed indeed corresponds to the amount of acetone produced.

Thus, the aerogel of the mixed oxide of nickel and aluminum (whose ratio Ni/Al = 3/5) which has undergone preliminary treatment is an exclusive catalyst for controlled oxidation which leads under the conditions indicated to methylacrolein and to acetone.

EXAMPLE 2

The second example illustrates the case of a catalyst comprising as a support a mixed metallic oxide and as a catalytic base an oxide, in this instance silicaalumina and nickel oxide.

The first step consists of obtaining alcogels by hydrolysis of alcoholic solutions of different organic compounds. As starting materials, there are used: methyl orthosilicate, secondary aluminum butylate and hydrated nickel acetate.

20 g of a solution of butanol containing 1.52 g of methyl orthosilicate and 0.285 g of secondary aluminum butylate are prepared in which there is added 5 g of a 20% by weight methanolic solution of hydrated nickel acetate and water in a sufficient amount to obtain stoechiometry of the hydrolysis reactions, taking into account the water introduced by the nickel salts, according to reactions (1) and (2) given in the first example and according to the reaction (6)

$$Si(OCH_3)_4 + 2 H_2O \rightarrow SiO_2 + 4 CH_3OH \quad (6)$$

Stirring is maintained for 5 minutes, then the container holding the gel is placed in the autoclave with 150 ml of butanol to proceed with the removal of the solvents under hypercritical conditions. The gelling of the solutions is carried out during the rise in temperature of the autoclave.

In this way, there is thus obtained a composite catalyst of 10% by weight with respect to the silica and which comprises a ratio of the number of atoms of nickel to the number of atoms of silicon and of aluminum equal to 2/5 (Ni/Si + Al).

In the same way there was prepared a family of catalysts having different percentages of alumina for a constant ratio Ni/Si + Al, and for a same percentage of alumina, catalysts were prepared of which the ratio Ni/Si + Al varies from 1/5 to 1.

The textural characteristics of these various solids are shown in Tables II and III.

TABLE II

| N° of Specimen | % $Al_2O_3$ | Ni/Si + Al | S $m^2/g$ | $V_p$ $cm^3/g$ | $V_{p_N}$ $cm^3/g$ |
|---|---|---|---|---|---|
| AS $N_1$ | 0 | 2/5 | 790 | 8.3 | 1.4 |
| AS $N_2$ | 1 | 2/5 | 570 | 8.7 | 0.8 |
| AS $N_3$ | 5 | 2/5 | 645 | 8.7 | 0.8 |
| AS $N_4$ | 10 | 2/5 | 520 | 8.6 | 0.7 |
| AS $N_5$ | 20 | 2/5 | 560 | 11.9 | 0.7 |

S specific surface measured by the BET method
$V_{p_N}$ porous volume measured by absorption of nitrogen at the temperature of liquid nitrogen (pores of a diameter less than 840 A)
$V_p$ porous volume measured by mercury porosimetry (pores of diameter greater than 580 A) The percentage by weight of alumina is determined with respect to the silica.

These results of Table II show that the specific surfaces as well as the microporous volumes remain practically constant when the concentration of alumina passes from 1 to 20%. On the other hand, it must be noted that the solid AS $N_1$ which is an aerogel not including alumina has a specific surface and a porous volume distinctly higher than those of the other solids.

TABLE III

| N° of specimen | Ni/Al + Si | S $m^2/g$ | $V_{p_N}$ $cm^3/g$ | $V_p$ $cm^3/g$ | % $Al_2O_3$ |
|---|---|---|---|---|---|
| AS $N_6$ | 1/5 | 600 | 0.76 | 7.3 | 10 |
| AS $N_4$ | 2/5 | 620 | 0.70 | 8.6 | 10 |
| AS $N_7$ | 3/5 | 830 | 0.63 | 7.1 | 10 |
| AS $N_8$ | 4/5 | 560 | 0.48 | 9 | 10 |
| AS $N_9$ | 1 | 560 | 0.48 | 8.2 | 10 |

The results of Table III show that increase in the proportion of nickel involves a reduction in the microporous volume probably due to filling of the micropores of the support. On the other hand, the specific area passes through a maximum corresponding to a porportion of the number of atoms of Ni to the number of atoms Si and of Al equal to 3/5.

Catalytic tests were carried out on the catalyst of which the weight percentage of alumina was 5%, and of which the ratio Ni/Si + Al is equal to 2/5; the oxidation reaction of isobutylene by oxygen was selected (dimerisation). The catalyst underwent preliminary activation treatment, it was desorbed under vacuum at 140°C, then treated with a flow of oxygen and of water vapour at atmospheric pressure and at a temperature in the neighbourhood of 300°C for 60 hours ($P_{H_2O}$ = 24 torr). The operation conditions of the catalytic tests were as follows:

| | |
|---|---|
| Pressure of reactants | 1 atmosphere |
| Composition of gases | 62.5% isobutylene |
| | 37.5% oxygen |
| Total flow rate of reactants | 1.6 l/h |
| Contact time (catalyst reactants) | 0.39 second |
| Temperature | 254°C. |

It is noted that the yield obtained for the principal products of the reaction is:

77% for diisopropylene (tri-methyl-2,2.4-pentene-1)
7.3% for acetone
11.1% for acetaldehyde
and 5% for other products such as isopropanol, methanol, and methylacrolein.

It is to be noted that no complete oxidation product (oxides of carbon) was detected in the course of the reaction.

The examples which follow relate to dispersions of metals on a support, the latter being constitutable by a single element or by two elements.

EXAMPLE 3

An alcoholic solution of secondary aluminum butylate and nickel acetate hydrated to 4 $H_2O$ was prepared. For this, 2.5 g of secondary aluminum butylate were dissolved in butanol-2, and it was made up to 20 g with said solvent, and there was added with stirring 5 g of a 20% by weight methanol solution of nickel acetate containing the water necessary for the stoechiometry of the hydrolysis reaction of the aluminum salt (taken into account that the water introduced by the nickel acetate). Precipitation takes place immediately, stirring is continued for 5 minutes, then the container is covered with a U-tube and it is placed in a 1 liter autoclave with 350 ml of methanol, the volume necessary to obtain hypercritical conditions. The reduction of the nickel takes place during the rise in temperature of the autoclave. As soon as the latter is closed, the dead volume is swept with a current of nitrogen, then the hydrogen inlet valves are closed when the pressure reached by the latter inside the autoclave is one atmosphere. It is heated to 270°C, then the solvent is removed, the apparatus is purged of the last alcohol vapours by a current of hydrogen, then the autoclave is allowed to cool to remove the solid aerogel.

In the present case, the ratio of the number of atoms of nickel to the number of atoms of alumina is equal to 2/5. In the same way, a family of catalysts of the same type was prepared for different ratios Ni/Al, namely: 1/5, 3/5, 4/5 and 1.

The aerogel obtained under the conditions described above have very superior textural characteristics. Its specific surface and its microporous volume, measured by nitrogen absorption at the temperature of liquid nitrogen, are respectively 500 $m^2/g$, 1.6 $cm^3/g$ and its macroporous volume measured by mercury porosimetry is equal to 10 $cm^3/g$. The metallic surface of the nickel, measured by hydrogen chemisorption at ambient temperature is then 160 $m^2/g$ of nickel.

Account can be better taken of the quality of the catalyst obtained by this method by comparing these values with those of conventional catalysts, such as Raney nickel for example whose specific surface is 80 $m^2/g$.

It was shown that the amount of water which is admitted at the moment of hydrolysis affects the final structure of the solids, and especially the areas occupied by the metal passing through a maximum when the stoechiometric conditions are respected. These relationships are shown in the Table IV.

The symbols S, $V_{PN}$ and $V_P$ have the same significance as those given with respect to Table II. As for $S_{Ni}$, its significance is as follows: surface occupied by the nickel, measured by hydrogen chemisorption.

The collapse of the structure of the aerogels which is produced with the increase in the amount of water introduced into the reaction medium is due to recrystallisation of the alumina support, facilitated by the presence of water during the rise in temperature of the autoclave. This reduction in the area available at the surface of the support involves a distinct reduction of the areas occupied by the metal.

The influence of the solvent used was also determined in preparing aerogels in other media, on one hand, in a homogeneous phase, by proceeding respectively with the hydrolysis of secondary aluminum butylate dissolved in butanol-2 as in the method described previously, or again by replacing by washing on a Soxlet the butanol-2 by methanol in the course of an additional operation coming directly after the abovesaid hydrolysis.

On the other hand, in heterogeneous phase by proceeding with hydrolysis of the aluminum butylate in a toluene-water medium.

The results of measurements carried out which are to be found in the Table below and study of the absorption isotherms permit the observation that the specific surfaces of the aerogels remain practically constant whatever the solvent used. The reduction in the microporous volume noted in the specimen of which the butanolic solvent was replaced by methanol, arises from the operations carried out on the alcogel and especially the change of solvent at the soxlet. It is to be noted, on the other hand, that the metallic surfaces are affected by the nature of the precipitating solvents. In fact, precipitation in a heterogeneous toluene-water medium involves a distinct reduction, of the area occupied by the nickel. Study of the X-ray spectra on two specimens enable the observation that the alumina supports are identical, but on the other hand the lines corresponding to the nickel are much more distinct and fine in the case of the aerogel precipitated in toluene than in the case of the aerogel precipitated in butanol, thus indicating the presence of much coarser crystallites of nickel in the first case and thus establishing the existance of a smaller metallic surface.

TABLE V

| N° of Specimen | S $m^2/g$ | $V_{PN}$ $cm^3/g$ | $V_P$ $cm^3/g$ | $S_{Ni}$ $m^2/g$ Ni |
|---|---|---|---|---|
| $NA_2$ bu Me | 450 | 0.72 | 11.9 | 57 |
| $NA_2$ Tol | 520 | 1.51 | 9.9 | 40 |
| $NA_2$ bu | 500 | 1.60 | 10 | 160 |

After having determined the influence of the amount of water introduced at the moment of hydrolysis, as

TABLE IV

| N° of Specimen | $H_2O$ | S $m^2/g$ | $V_{PN}$ $cm^3/g$ | $V_P$ $cm^3/g$ | $S_{Ni}$ $m^2/g$ Ni |
|---|---|---|---|---|---|
| $NA_1$ | introduced by the Ni salt | 520 | 1.1 | 9.3 | 110 |
| $NA_2$ | stoechiometry | 500 | 1.6 | 10 | 160 |
| $NA_3$ | 2 × stoechiometry | 210 | 0.8 | 8 | 40 |
| $NA_4$ | 4 × stoechiometry | 200 | 0.6 | 6.9 | 30 | well as the influence of the nature of the solvent on the textural qualities of the catalyst, the influence of the starting aluminum salt was studied, and as the other organometallic compound, the isopropylate was taken in particular.

This alcoholate not being soluble in butanol, nor in isopropanol, hydrolysis takes place after dissolving in toluene. The nickel salt used is the hydrated acetate and precipitation takes place at ambient temperature with vigorous stirring on account of the water-toluene heterogeneity.

The results obtained from the two alcoholates are shown in Table VI:

TABLE VI

| Specimen | S m²/g | $V_{P_N}$ cm³/g | $V_P$ cm³/g | $S_{Ni}$ m²/g Ni |
|---|---|---|---|---|
| NA₂ toluene isobutylate | 370 | 0.70 | 9.9 | 40 |
| NA₂ toluene isopropylate | 360 | 0.85 | 11.8 | 95 |

The following comparisons can be established: the precipitation of the gel from butylate or from isopropylate does not introduce important modifications of the porous texture (identical specific area and microporous volume). On the other hand, if the metallic surface of each of the two solids is considered, it appears that precipitation of the isopropylate in toluene facilites further the dispersion of the metallic nickel at the surface of the porous port. There can hence be obtained porous solids of very advantageous textures by hydrolysis in toluene of aluminum isopropylate (the nickel being then introduced in the form of a methanol solution of the hydrated acetate).

The activity of this type of catalyst was determined in the course of the following hydrogenolysis reaction of toluene:

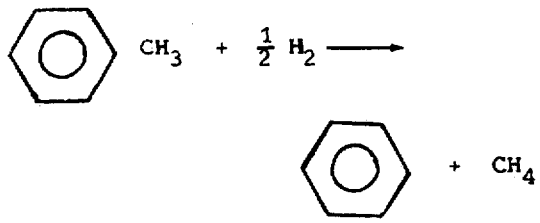

Catalytic tests on the initial reaction velocity, and the rate of splitting off from the ring were carried out; they were effected on two nickel-alumina aerogels whose ratio of the number of atoms of nickel to the number of atoms of aluminum is 2/5 and 3/5. They were carried out at a temperature of 325°C, with a pressure of hydrogen of 710 torr and of toluene of 50 torr. The gaseous flow rate was selected in such a way that the velocity observed was indeed that of the initial reaction velocity. The mass of catalyst which comes into play is about 10 mg; (which gives a conversion ratio less than 3%).

The activity shown by the initial velocity of the reaction $V_o$ is calculated according to the equasion:

$$V_o = \frac{1}{m} \cdot \frac{P_B}{760} \cdot \frac{D}{22400}$$

$m$: weight of catalyst in g
$P_B$: partial pressure of the benzine - (torr)
$D$: total flow rate emerging from the reaction (cm₃/s)
$V_o$: initial velocity (mole g⁻¹ s⁻¹)

It was thus calculated that after 16 hours of operation the activity only represented 25% of the activity observed 35 minutes after the introduction of the reactants.

The results which are shown in Table VII show that the catalysts possess a considerable specific activity with respect to the hydrogenolysis reaction of toluene. The slight increases in the ratio of splitting off from the ring shown by the tests being connected with a low percentage of degradation products.

TABLE VII

| Specimen | Molar Activity g⁻¹ s⁻¹ | Percentage of splitting off of the ring |
|---|---|---|
| NA₂ | 3.6.10⁻⁶ | 11% |
| NA₃ | 9.6.10⁻⁶ | 16% |

As a catalyst constituted by a metallic dispersion at the surface of a porous support, there will be given another example as follows where the support is constituted by two mineral oxides, alumina and magnesia.

The aerogels were obtained by hydrolysis of alcoholic solutions of secondary aluminum butylate, of magnesium methylate and of hydrated nickle acetate.

For this, 2.5 g of aluminum butylate were dissolved in a sufficient amount of butanol-2 to obtain 20 g of solution, then into this stirred solution were introduced methanolic solutions of magnesium methylate and hydrated nickel acetate in sufficient amount to obtain a mixture whose ratio of the number of atoms of nickel to the number of atoms of aluminum and of magnesium was equal to 3/5. The water was introduced so as to obtain just the amount necessary for stoechiometry of the hydrolysis reactions:

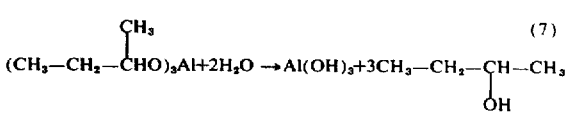

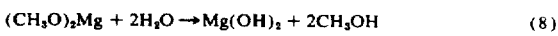

(CH₃O)₂Mg + 2H₂O → Mg(OH)₂ + 2CH₃OH          (8)

The results of measurements carried out on aerogels of increasing concentration in magnesia are to be found in Table VIII.

TABLE VIII

| Specimen | MgO | S m²/g | $V_{P_N}$ cm³/g | $V_P$ cm³/g | $S_{Ni}$ m²/g Ni |
|---|---|---|---|---|---|
| Am N₁ | 8.3% | 480 | 1.3 | 12.4 | 48 |
| AM N₂ | 11% | 500 | 1.3 | 18.5 | 89 |
| AM N₃ | 15.2% | 500 | 1.3 | 14.8 | 32 |
| AM N₄ | 20% | 450 | 1.3 | 17.2 | 29 |

Observation of these results as well as those of the nitrogen absorption desorption isotherms show that the specific areas and the microporous volumes remain constant when the concentration of magnesia increases up to 20%. If one considers the surfaces occupied by the metallic nickel, the latter pass through a high maximum corresponding to 11% of magnesia.

The influence of the concentration of nickel on the textural aspect of aerogels containing 11% of magnesia was hence consequently determined. The latter were prepared by introducing into alcoholic solutions of aluminum butylate and magnesium methylate, solutions more and more concentrated in hydrated nickel acetate in methanol, the amount of water introduced remaining always equal to the stoechiometric amount of the hydrolysis reactions.

The results obtained with these new aerogels are as follows:

TABLE IX

| Specimen | $\frac{(Ni)}{(mg)+(Al)}$ | S m²/g | $V_{p_N}$ cm³/g | $V_p$ cm³/g | $S_{Ni}$ m²/g Ni |
|---|---|---|---|---|---|
| AM N₄ | 1/5 | 950 | 2.36 | 7.8 | 61 |
| AM N₅ | 2/5 | 580 | 1.65 | 16.3 | 58 |
| AM N₂ | 3/5 | 500 | 1.3 | 18.5 | 89 |
| AM N₇ | 4/5 | 220 | 0.6 | 15 | 51 |
| AM N₈ | 1 | 220 | 0.6 | 11.1 | 34 |

It was noted that, when the concentration of nickel is little increased, it is possible to obtain solids of very developed porous texture. These textural properties then diminish gradually when the percentage of nickel increases. There is filling of the micropores of the solid, which involves at the same time a reduction in the specific area, of the microporous volume and of the metallic area.

If one compares the results obtained in the course of the two last examples, it can be assumed that the textural qualities are better in alumina-magnesia, nickel, catalysts at least as regards the specific surface and the porous volumes, which is in relationship with the presumed existance of a solid solution between the two mineral oxide supports. The dispersion of the metal on the support does not seem to be facilitated by the presence of magnesia in the solid although the metallic surfaces can be however relatively great.

We claim:

1. A method for the preparation of a composite catalyst, starting from a solution in a non-aqueous solvent of a compound of at least one transition metal and of a salt of at least one metal able to provide a refractory oxide, each of said compounds being selected among those of said metals which are both hydrolysable by water to form the corresponding hydroxides and soluble in said non-aqueous solvent, which method comprises adding to said solution an amount of water sufficient to cause hydrolysis of said salts and treating the reaction medium with a non-aqueous and volatile solvent in an amount and under conditions of temperature and pressure that result in the critical point of said solvent being reached and even exceeded thereby causing all the solvent to be in the form of vapor and removing the solvent vapor from said reaction medium.

2. Method according to claim 1, wherein the amount of water used for said hydrolysis corresponds substantially to that necessary for the stoichiometry of the reactions.

3. A method according to claim 1 wherein said hydrolysis is effected with the amount of water required by the stoichiometry of the hydrolysis reaction and wherein the reaction medium is heated in a closed autoclave, the amount of solvent used initially being such that the critical temperature can be reached and even exceeded under the corresponding pressure conditions.

4. Method according to claim 1, wherein the metals of the hydrolysable salts of the transition metals which are utilised belong to Group VIII of the Periodic Classification.

5. Method according to claim 1, wherein the salt of the abovesaid transition metal is a salt of nickel, of iron or of cobalt.

6. Method according to claim 1, wherein the salt of the said transition metal is a salt of nickel.

7. Method according to claim 1, wherein the salt of the abovesaid refractory metal is a salt of aluminum, of silicon or of magnesium.

8. Method according to claim 1, wherein the drying of the coprecipitate in the autoclave is effected in a reducing atmosphere.

9. Method according to claim 1, wherein the abovesaid salts are constituted by alcoholates or acetates of the metals concerned.

10. Method according to claim 1, wherein the hydrolysing medium is constituted by a homogeneous water-alcohol mixture, or a heterogeneous water-toluene mixture.

11. Method according to claim 1, wherein the ratio of the number of atoms of metal of the catalysing substance to the number of atoms of the refractory substance is comprised between 1/5 and 3/5.

12. Method according to claim 8, wherein the ratio of the number of atoms of metal of the catalysing substance to the number of atoms of metal of the refractory substance is comprised between 1/5 and 1/1.

* * * * *